(12) United States Patent
Speed et al.

(10) Patent No.: US 7,235,254 B1
(45) Date of Patent: Jun. 26, 2007

(54) POISONED STAKE DEVICE, METHOD OF MAKING AND METHOD OF USING

(76) Inventors: James E. Speed, 5738 Warwaoman Rd., Clayton, GA (US) 30525; Gail Speed, 5738 Warwaoman Rd., Clayton, GA (US) 30525

(*) Notice: Subject to any disclaimer, the term of this patent is extended or adjusted under 35 U.S.C. 154(b) by 710 days.

(21) Appl. No.: 10/646,041

(22) Filed: Aug. 22, 2003

(51) Int. Cl.
*A01N 25/34* (2006.01)

(52) U.S. Cl. ............... 424/409; 424/405; 424/411; 424/421; 424/703; 424/705; 424/731; 514/558

(58) Field of Classification Search ............... None
See application file for complete search history.

(56) References Cited

U.S. PATENT DOCUMENTS 1,296,771 A * 3/1919 Dady .................... 43/124
3,852,913 A * 12/1974 Clendinning et al. .......... 47/74
D324,558 S * 3/1992 Weiser et al. ............... D22/120
2003/0024169 A1* 2/2003 Kendall et al. ............... 51/297

OTHER PUBLICATIONS

Carvalho et al Caba # 92:49654 , Communicado Tecnio Centro Nacional de Pesquisa de Coco 1988 # 24 P 2.*

* cited by examiner

*Primary Examiner*—Neil S. Levy

(57) ABSTRACT

A method of making a poisoned stake device, the poisoned stake device and a method of using the poisoned stake device are disclosed. The method of making the poisoned stake device includes the steps of acquiring, adding, combining, curing, dispensing, filling, getting, mixing, pouring, procuring, removing, and scooping. The device is made from the method of making a poisoned stake device. The method of using the poisoned stake device includes the steps of discarding, identifying, inhibiting, obtaining, and removing so that burrowing mammal pest may be either killed or encouraged to vacate the vicinity of their burrowed hill.

12 Claims, 2 Drawing Sheets

POISONED STAKE DEVICE, METHOD OF MAKING AND METHOD OF USING

FIELD OF THE INVENTION

The present invention relates to poisons, more particularly, to a poisoned stake device, a method of making, and method of using the poisoned stake device in eradicating burrowing mammal pests, such as moles, voles, gophers and alike.

BACKGROUND OF THE INVENTION

Burrowing mammal pest have continually been a commonly encountered pest at well tendered lawns and golf courses. It has been estimated that burrowing mammal pest such as mole, have caused millions of dollars of damage to these lawns and golf courses.

A wide variety of poisons is currently available on the commercial market and an even larger number of these types of devices are known in the art of poisons, for example, the gopher poisoner disclosed by Dady in U.S. Pat. No. 1,296,771; the method and articles for killing termites disclosed by Browdy in U.S. Pat. No. 5,564,222; the termiticide bait tube for in ground application in U.S. Pat. No. 6,003,266; the article for release of repellents and insecticides disclosed by Matson in U.S. Pat. No. 6,093,413; the mole chaser disclosed by Jan in U.S. Pat. No. 6,157,594; and the rodent deterrent stake disclosed by Weiser et al. in U.S. Pat. No. D324,558.

While all of the above-described devices fulfill their respective, particular objectives and requirements, the aforementioned patents do not describe a method of making a poisoned stake device that includes the steps of acquiring, adding, combining, curing, dispensing, filling, getting, mixing, pouring, procuring, removing, and scooping. This combination of elements would specifically match the user's particular individual needs of making it possible to conveniently construct a repellant which is capable of inhibiting burrowing mammal pest from the vicinity of their burrowed hill. The above-described patents make no provision for a method of making a poisoned stake device that includes the steps of acquiring, adding, combining, curing, dispensing, filling, getting, mixing, pouring, procuring, removing, and scooping.

Therefore, a need exists for a new and improved method of making a poisoned stake device made from the steps of acquiring, adding, combining, curing, dispensing, filling, getting, mixing, pouring, procuring, removing, and scooping. In this respect, the poisoned stake device according to the present invention substantially departs from the conventional concepts and designs of the prior art, and in doing so provides an apparatus primarily developed for the purpose of providing a convenient means for constructing a repellant which is capable of inhibiting burrowing mammal pest from the vicinity of their burrowed hill.

SUMMARY OF THE INVENTION

The present poisoned stake device, the method of making a poisoned stake device, and the method of using same, according to the principles of the present invention, overcomes the shortcomings of the prior art by providing a novel and nonobvious method of making, the poisoned stake device, and method of using the same. The method of making the poisoned stake device includes the steps of acquiring, adding, combining, curing, dispensing, filling, getting, mixing, pouring, procuring, removing, and scooping. The device is made from the method of making a poisoned stake device. The method of using the poisoned stake device includes the steps of discarding, identifying, inhibiting, obtaining, and removing so that burrowing mammal pest may be either killed or encouraged to vacate the vicinity of their burrowed hill.

In view of the foregoing disadvantages inherent in the known type methods of making poisoned stake devices now present in the prior art, the present invention provides an improved poisoned stake device, which will be described subsequently in great detail, is to provide a new and improved poisoned stake device which is not anticipated, rendered obvious, suggested, or even implied by the prior art, either alone or in any combination thereof.

To attain this, the present invention essentially comprises a method of making a poisoned stake device, which includes the steps of acquiring, adding, combining, curing, dispensing, filling, getting, mixing, pouring, procuring, removing, and scooping.

There has thus been outlined, rather broadly, the more important features of the invention in order that the detailed description thereof that follows may be better understood, and in order that the present contribution of the art may be better appreciated.

The method of making invention may also include an additional step of sealing the poisoned stake device within a container. There are of course, additional features of the invention that will be described hereinafter and which will form the subject matter of the claims attached.

Numerous objects, features and advantages of the present invention will be readily apparent to those of ordinary skill in the art upon reading of the following detailed description of presently preferred, but nonetheless illustrative, embodiments of the present invention when taken in conjunction with the accompany drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved poisoned stake device that has all the advantages of the prior art poisoned stake device and none of the disadvantages.

It is another object of the present invention to provide a new and improved poisoned stake device that may be easily and efficiently manufactured and marketed.

An even further object of the present invention is to provide a new and improved poisoned stake device that has a low cost of manufacture with regard to both materials and labor, and which accordingly is then susceptible of low prices of sale to the consuming public, thereby making such multipurpose storage unit and system economically available to the buying public.

Still another object of the present invention is to provide a new poisoned stake device that provides in the apparatuses and methods of the prior art some of the advantages thererof, while simultaneously overcoming some of the disadvantages normally associated therewith.

Even still another object of the present invention is to provide a method of making a poisoned stake device that includes the steps of acquiring, adding, combining, curing, dispensing, filling, getting, mixing, pouring, procuring, removing, and scooping. This combination of elements makes it possible to conveniently construct a repellant which is capable of inhibiting burrowing mammal pest from the vicinity of their burrowed hill.

Still another object of the present invention is to provide the device is made from the method of making a poisoned stake device.

Lastly, it is an object of the present invention to provide a new and improved method of using comprising the steps of discarding, identifying, inhibiting, obtaining, and removing so that burrowing mammal pests may be either killed or encouraged to vacate the vicinity of their burrowed hill.

Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and description matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description males reference to the annexed drawings wherein.

The same reference numerals refer to the same parts throughout the various figures.

DETAILED DESCRIPTION OF THE PREFERRED EMBODIMENT

Figure 1:
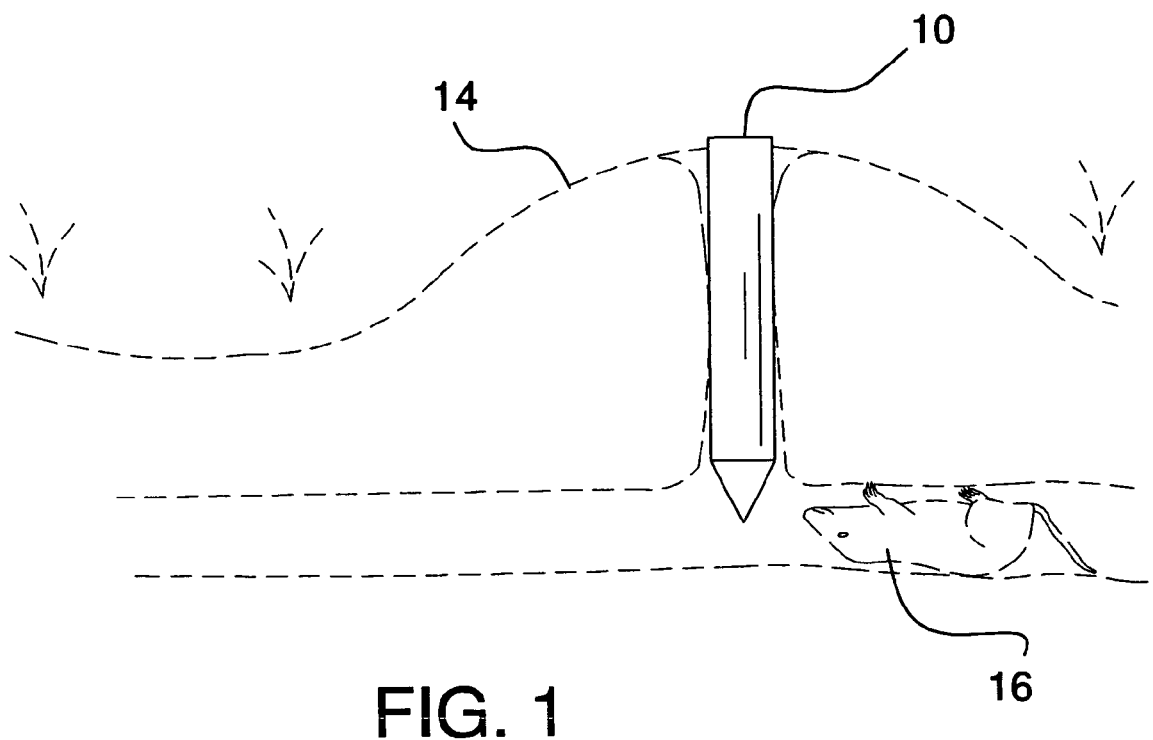
FIG. 1 is a perspective view of an preferred embodiment of the poisoned stake device constructed in accordance with the principles of the present invention.
Figure 2:
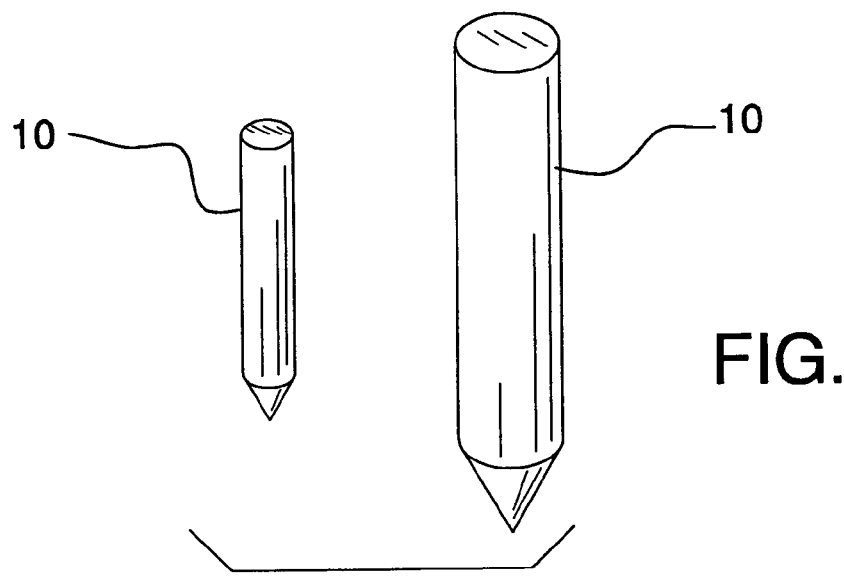
FIG. 2 is a perspective view of a preferred embodiment of the poisoned stake device of the present invention.
Figure 3:
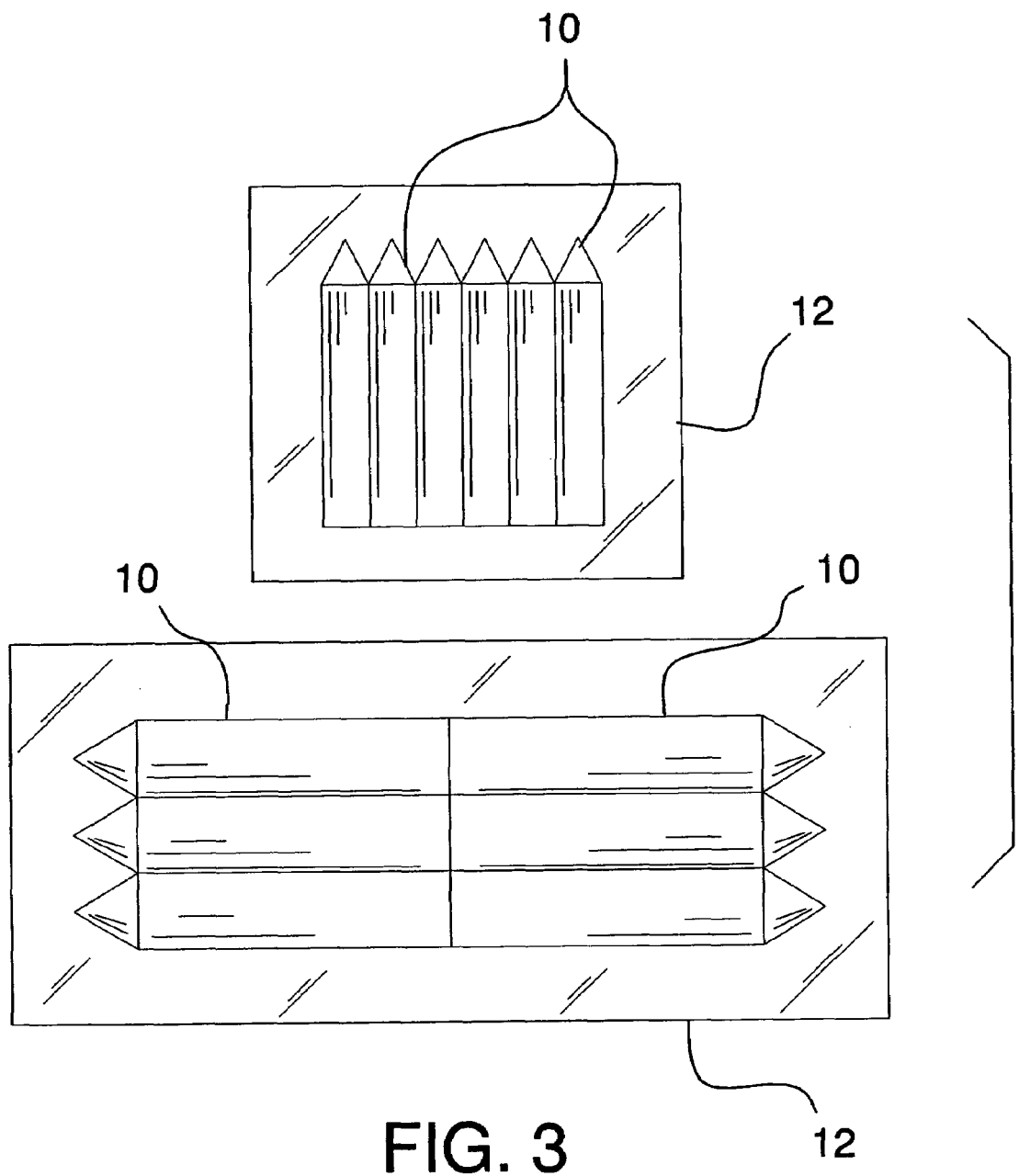
FIG. 3 is a top plan view of a preferred embodiment of the poisoned stake device of the present invention wrapped in a container.

Referring now to the drawings, and in particular FIGS. 1 to 3 thereof, one preferred embodiment of the present device invention is shown and generally designated by the reference numeral 10. One preferred method of making a poisoned stake device 10 comprising the steps of acquiring, adding, combining, curing, dispensing, filling, getting, mixing, pouring, procuring, removing, and scooping. The procuring step comprises procuring a filler composition containing about 40-90% w/w ground dried clay and about 10-60% w/w crushed limestone. The getting step comprises getting a mixing chamber. The adding step comprises adding the filler composition in an amount of about 30% to about 50% v/v into the mixing chamber. The scooping step comprises scooping plaster of Paris in an amount of about 30% to about 50% v/v into the mixing chamber. The dispensing step comprises dispensing sulfur in an amount of about 0.05% to about 2% v/v into the mixing chamber. The pouring step comprises pouring caster oil in an amount of about 1 to about 7% v/v into the mixing chamber. The combining step comprises combining water in an amount of about 15% to about 25% v/v into the mixing chamber. The mixing step comprises mixing together the filler composition, the plaster of Paris, the sulfur, the caster oil, and the water in the mixing chamber into a moistened composite. The acquiring step comprises acquiring a die with an internal hollow mold chamber, wherein said internal hollow mold chamber of the die includes an elongated cylindrical spike shape having a pointed end and a blunt end. The filling step comprises filling the internal hollow mold chamber of the die with an aliquot of the moistened composite. The removing step comprises removing a spiked shaped moistened composite from the die. The curing step comprises curing the spiked shaped moistened composite into a hardened poisoned stake device 10 by exposing the spiked shaped moistened composite to ambient air for at least two hours.

An optional step of sealing may be added to the method of making the poisoned stake device 10 wherein the sealing step comprises the hardened poisoned stake device 10 in a container 12. The container 12 may be made of any commercially available material, such as plastic, paper, or metal. The plastic of the container 12 may be selected from the group consisting of rubber, neoprene, polyvinyl chloride, polyester, polyethylene, polypropylene, polyurethanes, polyacryls, polymethacryls, cellulosic polymers, styrene-acryl copolymers, polystyrene-polyacryl mixtures, polysiloxanes, urethane-acryl copolymers, siloxane-urethane copolymers, polyurethane-polymethacryl mixtures, silicone-acryl copolymers, vinyl acetate polymers, and mixtures thereof. The metal of the container 12 may be made of aluminum foil.

A more preferred embodiment of the method of making the poisoned stake device 10 includes: the filler composition of said adding step is in an amount of about 35% to about 45% v/v in the mixing chamber; the plaster of Paris in said scooping step is in an amount of about 35% to about 45% v/v in the mixing chamber; the sulfur in said dispensing step is in an amount of about 0.1% to about 1% v/v in the mixing chamber; the caster oil in said pouring step is an amount of about 3% to about 5% v/v in the mixing chamber; and the water in said combining step is in an amount of about 17% to about 21% v/v in the mixing chamber.

An even more preferred embodiment of the method of making the poisoned stake device 10 includes: the filler composition of said adding step is in an amount of about 38.4% v/v in the mixing chamber; the plaster of Paris in said scooping step is in an amount of about 38.4% v/v in the mixing chamber; the sulfur in said dispensing step is in an amount of about 0.2% v/v in the mixing chamber; the caster oil in said pouring step is an amount of about 4% v/v in the mixing chamber; and the water in said combining step is in an amount of about 19% v/v in the mixing chamber.

A most preferred embodiment of the method of making the poisoned stake device 10 includes: the filler composition of said adding step is in ah amount of about 2 cups in the mixing chamber; the plaster of Paris in said scooping step is in an amount of about 2 cups in the mixing chamber; the sulfur in said dispensing step is in an amount of about one half teaspoon in the mixing chamber; the caster oil in said pouring step is an amount of about 9 teaspoons in the mixing chamber; and the water in said combining step is in an amount of about 2 cups in the mixing chamber.

The filler composition may be any commercially available material as long as it contains about 40-90% w/w ground dried clay and about 10-60% w/w crushed limestone. One preferred configuration is that the filler composition is a commercially available cat litter. Another preferred configuration is that the ground dried clay has a particle size of about 8/45 mesh and the crushed limestone has a particle size of about 16/25 mesh.

One preferred embodiment of a poisoned stake device 10 comprising the poisoned stake device 10 made from the method of making the poisoned stake device 10 as disclosed in Claim 1. The geometric size of the poisoned stake device 10 may be any geometric shape, such as measuring about 6 inches long and about 1 inch in diameter or by measuring about 4 inches long and about ½ inch in diameter.

One preferred method of using a poisoned stake device 10, said method using the stake comprising the steps of: discarding, identifying, inhibiting, obtaining, and removing. The obtaining step comprises obtaining the poisoned stake device 10 sealed in the container 12 made from the method of claim 2. The identifying step comprises identifying a burrow hill 14 in a field associated with a burrowing mammal pest 16. The removing step comprises removing the container 12 sealing the hardened poisoned stake device 10. The discarding step comprises discarding the container 12 into a trash receptacle. The inhibiting step comprises inhibiting the burrowing mammal pest 16 by depositing a portion of the poisoned stake device 10 at the burrow hill 14.

One preferred configuration of the inhibiting step of the method of using the poisoned stake device 10 comprises inserting the poisoned stake device 10 into the burrow hill 14. Another preferred configuration of the inhibiting step of the method of using the poined stake device 10 comprises crumbling the poisoned stake into a plurality of crumbs and pouring the crumbs onto the burrow hill 14. The inhibiting step may result in directly killing the burrowing mammal pest 16 or by forcing the burrowing mammal pest 16 to vacate from the vicinity of the hill 14.

The method of using the poisoned stake device 10 is directed to any known burrowing mammal pest 16 such as those selected from the group consisting of a mole, a shrew, a vole, a gopher, a rabbit, an armadillo, a chipmunk, and a squirrel Referring now to FIG. 1 which depicts a perspective view of an preferred embodiment of the poisoned stake device 10 showing the device 10 inserted within a hill 14 occupied by a burrowing pest, i.e., a mole, wherein the pest 16 is subsequently killed from the device 10.

Referring now to FIG. 2 which depicts a perspective view of a preferred embodiment of the poisoned stake device 10 showing that the stake may be made for use in eradicating a small and larger sized for burrowing mammal pests.

Referring now to FIG. 3 which depicts a top plan view of a preferred embodiment of the poisoned stake device 10 showing that the device 10 may be wrapped in a container 12.

As to the manner of usage and operation of the present invention, the same should be apparent from the above description. Accordingly, no further discussion relating to the manner of usage and operation will be provided.

While a preferred embodiment of the poisoned stake device has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Throughout this specification, unless the context requires otherwise, the word "comprise" or variations such as "comprises" or "comprising" or the term "includes" or variations, thereof, or the term "having" or variations, thereof will be understood to imply the inclusion of a stated element or integer or group of elements or integers but not the exclusion of any other element or integer or group of elements or integers. In this regard, in construing the claim scope, an embodiment where one or more features is added to any of the claims is to be regarded as within the scope of the invention given that the essential features of the invention as claimed are included in such an embodiment.

Those skilled in the art will appreciate that the invention described herein is susceptible to variations and modifications other than those specifically described. It is to be understood that the invention includes all such variations and modifications which fall within its spirit and scope. The invention also includes all of the steps, features, compositions and compounds referred to or indicated in this specification, individually or collectively, and any and all combinations of any two or more of said steps or features.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications' and equivalents may be resorted to, falling within the scope of the invention.

What is claimed as being new and desired to be protected by Letters Patent of the United States is as follows:

1. A method of making a poisoned stake device comprising the steps of procuring a filler composition containing about 40-90% w/w ground dried clay and about 10-60% w/w crushed limestone;
   getting a mixing chamber;
   adding the filler composition in an amount of about 30% to about 50% v/v into the mixing chamber;
   scooping plaster of Paris in an amount of about 30% to about 50% v/v into the mixing chamber;
   dispensing sulfur in an amount of about 0.05% to about 2% v/v into the mixing chamber;
   pouring caster oil in an amount of about 1 to about 7% v/v into the mixing chamber;
   combining water in an amount of about 15% to about 25% v/v into the mixing chamber;

mixing together the filler composition, the plaster of Paris, the sulfur, the caster oil, and the water in the mixing chamber into a moistened composite;

acquiring a die with an internal hollow mold chamber, wherein said internal hollow mold chamber of the die includes an elongated cylindrical spike shape having a pointed end and a blunt end;

filling the internal hollow mold chamber of the die with an aliquot of the moistened composite;

removing a spiked shaped moistened composite from the die; and curing the spiked shaped moistened composite into a hardened poisoned stake device by exposing the spiked shaped moistened composite to ambient air for at least two hours.

2. The method of claim 1 further comprising sealing the hardened poisoned stake device in a container.

3. The method of claim 2 wherein said container is made of plastic selected from the group consisting of rubber, neoprene, polyvinyl chloride, polyester, polyethylene, polypropylene, polyurethanes, polyacryls, polymethacryls, cellulosic polymers, styrene-acryl copolymers, polystyrene-polyacryl mixtures, polysiloxanes, urethane-acryl copolymers, siloxane-urethane copolymers, polyurethane-polymethacryl mixtures, silicone-acryl copolymers, vinyl acetate polymers, and mixtures thereof.

4. The method of claim 2 wherein said container is made of paper.

5. The method of claim 2 wherein said container is made of aluminum foil.

6. The method of claim 1 wherein
the filler composition of said adding step is in an amount of about 35% to about 45% v/v in the mixing chamber;
the plaster of Paris in said scooping step is in an amount of about 35% to about 45% v/v in the mixing chamber;
the sulfur in said dispensing step is in an amount of about 0.1% to about 1% v/v in the mixing chamber;
the caster oil in said pouring step is in an amount of about 3% to about 5% v/v in the mixing chamber; and
the water in said combining step is in an amount of about 17% to about 21% v/v in the mixing chamber.

7. The method of claim 1 wherein
the filler composition of said adding step is in an amount of about 38.4% v/v in the mixing chamber;
the plaster of Paris in said scooping step is in an amount of about 38.4% v/v in the mixing chamber;
the sulfur in said dispensing step is in an amount of about 0.2% v/v in the mixing chamber;
the caster oil in said pouring step is in an amount of about 4% v/v in the mixing chamber, and
the water in said combining step is in an amount of about 19% v/v in the mixing chamber.

8. The method of claim 1 wherein
the filler composition of said adding step is in an amount of about 2 cups in the mixing chamber;
the plaster of Paris in said scooping step is in an amount of about 2 cups in the mixing chamber;
the sulfur in said dispensing step is in an amount of about one half teaspoon in the mixing chamber;
the caster oil in said pouring step is in an amount of about 9 teaspoons in the mixing chamber; and
the water in said combining step is in an amount of about 2 cups in the mixing chamber.

9. The method of claim 1 wherein the ground dried clay has a particle size of about 8/45 mesh and the crushed limestone has a particle size of about 16/25 mesh.

10. A poisoned stake device comprising the poisoned stake device made from the method of claim 1.

11. The device of claim 10 wherein said devices measures about 4 inches long and about ½ inch in diameter.

12. The device of claim 10 wherein said device measures about 6 inches long and about 1 inch in diameter.

* * * * *